US011078456B2

United States Patent
Xu et al.

(10) Patent No.: US 11,078,456 B2
(45) Date of Patent: Aug. 3, 2021

(54) FUSARIUM SOLANI AND USE OF SAME IN PREVENTION AND TREATMENT OF SOUTHERN BLIGHT OF DENDROBIUM OFFICINALE KIMURA ET MIGO

(71) Applicant: JIANGSU VOCATIONAL COLLEGE OF AGRICULTURE AND FORESTRY, Zhenjiang (CN)

(72) Inventors: Chao Xu, Zhenjiang (CN); Hongyan Zhang, Zhenjiang (CN); Hetong Yang, Zhenjiang (CN); Gangjun Xi, Zhenjiang (CN); Kai Zheng, Zhenjiang (CN); Jun Shi, Zhenjiang (CN)

(73) Assignee: JIANGSU VOCATIONAL COLLEGE OF AGRICULTURE AND FORESTRY, Zhenjiang (CN)

( * ) Notice: Subject to any disclaimer, the term of this patent is extended or adjusted under 35 U.S.C. 154(b) by 0 days.

(21) Appl. No.: 16/650,975

(22) PCT Filed: Aug. 13, 2018

(86) PCT No.: PCT/CN2018/100274
§ 371 (c)(1),
(2) Date: Mar. 26, 2020

(87) PCT Pub. No.: WO2019/062355
PCT Pub. Date: Apr. 4, 2019

(65) Prior Publication Data
US 2020/0281214 A1    Sep. 10, 2020

(30) Foreign Application Priority Data
Sep. 30, 2017  (CN) .......................... 201710916814.3

(51) Int. Cl.
*C12N 1/14* (2006.01)
*A01N 63/30* (2020.01)
*C12R 1/77* (2006.01)

(52) U.S. Cl.
CPC ............... *C12N 1/14* (2013.01); *A01N 63/30* (2020.01); *C12N 1/145* (2021.05); *C12R 2001/77* (2021.05)

(58) Field of Classification Search
CPC .. C12N 1/14; C12N 1/145; C12N 1/20; C12R 2001/77; A01N 63/30
See application file for complete search history.

(56) References Cited

PUBLICATIONS

Sugiura et al., Medical Mycology, 2003, vol. 41, p. 241-247.*

* cited by examiner

*Primary Examiner* — Kade Ariani
(74) *Attorney, Agent, or Firm* — CBM Patent Consulting, LLC

(57) ABSTRACT

A *Fusarium solani* strain and a use thereof in the control of southern blight disease of *Dendrobium officinale* Kimura et Migo, and the strain JSNL007-2 has been identified as *Fusarium solani* and has been deposited in China Center for Type Culture Collection on Mar. 10, 2017 with a deposit number of CGMCC NO. 13687. The *Fusarium solani* JSNL007-2 of the present invention has a significant effect on the disease resistance of *Dendrobium officinale* Kimura et Migo, especially for improving the ability of *Dendrobium officinale* Kimura et Migo to resist southern blight disease, and has a certain effect on reducing the use of chemical pesticides, which is an important means to ensure food safety.

4 Claims, 2 Drawing Sheets
Specification includes a Sequence Listing.

SEQUENCE LISTING

<160> NUMBER OF SEQ ID NOS: 1

<210> SEQ ID NO 1
<211> LENGTH: 502
<212> TYPE: DNA
<213> ORGANISM: Artificial Sequence
<220> FEATURE:
<223> OTHER INFORMATION: It is synthesized.

<400> SEQUENCE: 1

```
aagttacctg tcatacggca tggccgcgcc gctctccagt tgcgaggtgt tagctactac      60
gcaatggaag ctgcggcggg accgccactg tatttgaggg acggcgtgtg cccacagggg     120
gcttccgccg atccccaacg ccaggcccgg gggcctgagg gttgtaatga cgctcgaaca     180
ggcatgcccg ccagaatact ggcgggcgca atgtgcgttc aaagattcga tgattcactg     240
aattctgcaa ttcacattac ttatcgcatt tcgctgcgtt cttcatcgat gccagagcca     300
agagatccgt tgttgaaagt tttaatttat ttgcttgttt actcagaaaa acattataaa     360
aacagagtta ggggtcctct ggcggggggcg gcccgttgtt acagggccgt ctgttcccgc     420
cgaagcaacg ttttaggtat gttcacaggg ttgatgagtt gtataactcg gtaatgatcc     480
ctccgcaggt cacactacgg aa                                              502
```

FUSARIUM SOLANI AND USE OF SAME IN PREVENTION AND TREATMENT OF SOUTHERN BLIGHT OF DENDROBIUM OFFICINALE KIMURA ET MIGO

TECHNICAL FIELD

The present invention belongs to the technical field of microorganisms, and particularly relates to a *Fusarium solani* strain and use thereof in the control of southern blight disease of *Dendrobium officinale* Kimura et Migo.

BACKGROUND

*Dendrobium* is a perennial herb of the orchidaceae family, with a total of more than 1,500 species worldwide. The *dendrobium* contained is divided two categories by the 2010 edition of the Chinese Pharmacopoeia, namely *dendrobium* and *Dendrobium officinale* Kimura et Migo which has very good nourishing and health preserving effects in addition to good medicinal effects. *Dendrobium officinale* Kimura et Migo has a small leaf area, low photosynthetic intensity, and strict requirements for the growth environment, and grows on large trunks and between stone walls and cracks, so it grows very slowly. Due to excessive excavation and destruction of the ecological environment, *Dendrobium* has been listed as one of the endangered protected medicinal species in China. At present, the market demand for *Dendrobium officinale* Kimura et Migo mainly depends on artificial cultivation, but artificially cultivated *Dendrobium officinale* Kimura et Migo has a slow growth rate, low average yield, serious disease occurrence, and the control of diseases still mainly depends on pesticides. From the perspective of protecting the ecological environment and food safety, as a valuable Chinese medicine, *Dendrobium officinale* Kimura et Migo should reduce the amount of pesticide used as much as possible. Reasonable utilization of fungal resources, improving the disease resistance of *Dendrobium officinale* Kimura et Migo, and reducing the application amount of chemical pesticide to a certain extent are also in line with the sustainable development strategy of agriculture. Therefore, research on biocontrol agents have become an important direction for *Dendrobium officinale* Kimura et Migo industry.

Southern blight disease, also known as sclerotium root rot disease and sclerotium seed blight disease, endangers the roots and stems of seedlings and young trees. Sclerotium of the southern blight disease overwinters on the substrates and plant residues, and can develop from late spring to late autumn. In bed troughs with excessive planting density, thunderstorm weather with high temperature and humidity, it is more susceptible to disease, especially under the condition that the substrate is acidic (PH value 3-5), the disease is most serious. The disease has a rapid onset, rapid transmission, and large devastation. At present, the control of southern blight disease of *Dendrobium officinale* Kimura et Migo is by chemical pesticides, which is easy to harm *Dendrobium officinale* Kimura et Migo. How to effectively control southern blight disease through biological control methods has become one of the current research hotspots in *Dendrobium officinale* Kimura et Migo industry.

SUMMARY

Objectives of the present invention: in view of the problems existing in the prior art, the present invention provides a biocontrol strain JSNL007-2 of *Dendrobium officinale* Kimura et Migo against southern blight disease for improving the ability of *Dendrobium officinale* Kimura et Migo to resist southern blight disease. Another objective of the present invention is to provide an inoculant produced by the strain and a use thereof, and the solid microbial inoculant prepared by the strain can significantly improve the ability of *Dendrobium officinale* Kimura et Migo to resist southern blight disease.

Technical solution: in order to achieve the above objectives, a *Fusarium solani* strain named as JSar007-2 according to the present invention, has been deposited in China Center for Type Culture Collection (address: Beijing No. 3 Courtyard, No. 1 Beichen West Road, Chaoyang District, Institute of Microbiology, Chinese Academy of Sciences, Postcode: 100101) on Mar. 10, 2017 with a deposit number of CGMCC NO. 13687. The strain was isolated and screened from plants with good growth conditions in the *Dendrobium officinale* Kimura et Migo planting area in Jurong City, Jiangsu Province in March 2015. The main biological characteristics of the strain JSNL007-2 are: the front mycelia are off-white, fleece, and are attached to the surface of the substrate; the reverse mycelia are white to pale yellow with slight pigmentation.

A use of the strain JSNL007-2 of the present invention in the control of southern blight disease of *Dendrobium officinale* Kimura et Migo.

A microbial inoculant produced by the strain JSNL007-2 according to the present invention.

A preparation method for the microbial inoculant by using the strain JSNL007-2 according to the present invention, wherein the microbial inoculant is prepared by the following steps:

(1) preparing a solid medium using cottonseed husk dregs as culture substrate, ammonium nitrate as exogenous nitrogen source, and sucrose as exogenous carbon source, sterilizing, and inoculating the *Fusarium solani* strain JSNL007-2;

(2) culturing for 5-8 days under a condition of 25-30° C., 8 hours of light and 16 hours of darkness per day, and pH of 6.0-6.5;

(3) cutting the solid microbial inoculant cultured in step (2) into 1-1.5 cm3 blocks and setting aside.

Wherein the sterilizing condition in step (1) is sterilizing for 20-25 minutes under a condition of 121° C. and a high pressure of 101.3 kPa.

A use of the microbial inoculant produced by the strain JSNL007-2 according to the present invention in improving the ability of *Dendrobium officinale* Kimura et Migo to resist southern blight disease.

Wherein the specific steps of the use are: inoculating the solid microbial inoculant on the cultivation substrate surface of the *Dendrobium officinale* Kimura et Migo seedling, and the inoculation amount of the solid inoculant per *Dendrobium officinale* Kimura et Migo seedling is 5-8 g.

Further, the relative water content of the substrate is maintained above 60% for 6-10 days after the solid microbial inoculant is inoculated on the cultivation substrate surface of the *Dendrobium officinale* Kimura et Migo seedling.

Beneficial effects: compared with the prior art, the advantages of the present invention are:

(1) the *Fusarium solani* strain JSNL007-2 of the present invention has a significant effect on the disease resistance of *Dendrobium officinale* Kimura et Migo, especially for improving the ability of *Dendrobium officinale* Kimura et Migo to resist southern blight disease, and has a certain effect on reducing the use of chemical pesticides, which is an important means to ensure food safety.

(2) the microbial inoculant produced by the *Fusarium solani* JSNL007-2 can significantly improve the ability of *Dendrobium officinale* Kimura et Migo to resist southern blight disease, and has simple culture conditions, is easy to store and easy for industrial production, and has good development and application prospects.

DETAILED DESCRIPTION

The present invention is further illustrated below with reference to the drawings and examples.

Example 1

Figure 1:
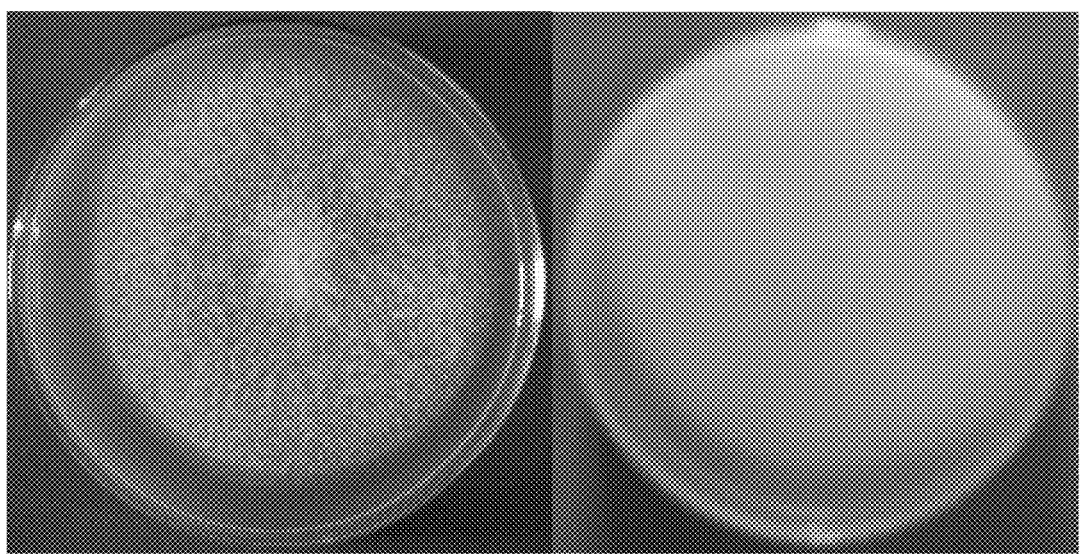
FIG. 1 is a colony photograph of the strain JSNL007-2 of the present invention.

A southern blight disease resistant strain JSNL007-2 of *Dendrobium officinale* Kimura et Migo is isolated and screened from plants with good growth conditions in the *Dendrobium officinale* Kimura et Migo planting area in Jurong City, Jiangsu Province, and cultured on a PDA plate, of which the front mycelia are off-white, fleece, and are attached to the surface of the substrate; the reverse mycelia are white to pale yellow with slight pigmentation, as shown in FIG. 1.

The full sequence of the ITS region of the strain JSNL007-2 is amplified and sequenced, and the full sequence of the rDNA ITS sequence obtained by PCR amplification is shown in SEQ ID No 1. By alignment on genebank, the results show that the strain JSNL007-2 has the closest homology with *Fusarium solani* strain, and has 99% homology with the strains *Fusarium solani* LYF019 and *Fusarium solani* CDR3P2F2, combining the morphological and physiological and biochemical characteristics, the strain JSNL007-2 is initially identified as *Fusarium solani* and named as *Fusarium solani* JSNL007-2, which belongs to *Fusarium* genus of Tuberculariaceae of Fungi Imperfecti subgenus. The strain JSNL007-2 has been deposited in China Center for Type Culture Collection of Institute of Microbiology, Chinese Academy of Sciences located in Beijing, China, on Mar. 10, 2017 with a deposit number of CGMCC NO. 13687.

Example 2

The microbial inoculant produced by the *Fusarium solani* JSNL007-2:

(1) preparing a solid medium using cottonseed husk dregs as culture substrate, ammonium nitrate as exogenous nitrogen source, and sucrose as exogenous carbon source, which was put into a autoclaving bag to sterilize for 20-25 minutes under a condition of 121° C. and a high pressure of 101.3 kPa, after the medium is cooled, inoculating the *Fusarium solani* strain JSNL007-2 under sterile conditions, and then performing artificial culture;

(2) specific culture conditions for artificial culture are culturing for 5-8 days under a condition of 25-30° C., 8 hours of light and 16 hours of darkness per day, and pH of 6.0-6.5;

(3) cutting the solid microbial inoculant cultured in step (2) into 1-1.5 cm3 blocks and setting aside.

Example 3

Effect analysis of the microbial inoculant produced by the *Fusarium solani* JSNL007-2 on the ability of *Dendrobium officinale* Kimura et Migo to resist southern blight disease.

(1) Artificial culture on PDA medium to obtain the sclerotia of southern blight disease pathogen;

(2) inoculating the solid microbial inoculant cultured in Example 2 and the sclerotia of southern blight disease pathogen cultured in step (1) simultaneously on the cultivation substrate surface of the *Dendrobium officinale* Kimura et Migo seedling, in which the inoculation amount of the solid inoculant per *Dendrobium officinale* Kimura et Migo seedling is 5-8 g, and the number of the sclerotia of southern blight disease pathogen is 10;

(3) after applying the inoculant, managing the *Dendrobium officinale* Kimura et Migo plants tested in step (2) under the same conditions, wherein the relative water content of the substrate is maintained above 60% for 6-10 days to ensure that the mycelia survive in the substrate;

the temperature in the greenhouse is 28-30° C., the humidity is 40%-50%, each treatment is 100 strains, and three groups are repeated; at the same time, plants inoculated with only the sclerotia of southern blight disease pathogen and without *Fusarium solani* JSNL007-2 solid inoculant are used as controls (CK).

(4) Monitoring the incidence degree, statistical incidence, and incidence index of southern blight disease every day after inoculation.

Diseased plants grading criteria: disease grading is mainly based on the number of rotten roots after inoculation, and the initial grading criteria are:

0: normal;

I: there are a few rotten roots;

II: the number of rotten roots accounts for less than ¼ of the total number of roots;

III: the number of rotten roots accounts for ¼-½ of the total number of roots;

IV: the number of rotten roots accounts for ½-¾ of the total number of roots;

IV: the number of rotten roots accounts for more than ¾ of the total number of roots.

Diseased index=Σ(number of diseased plants at each grading×representative value of the grading)× 100/(total number of plants×representative value of the highest grading);

Diseased rate=(number of diseased plants/number of inoculated plants)×100%.

Figure 2:
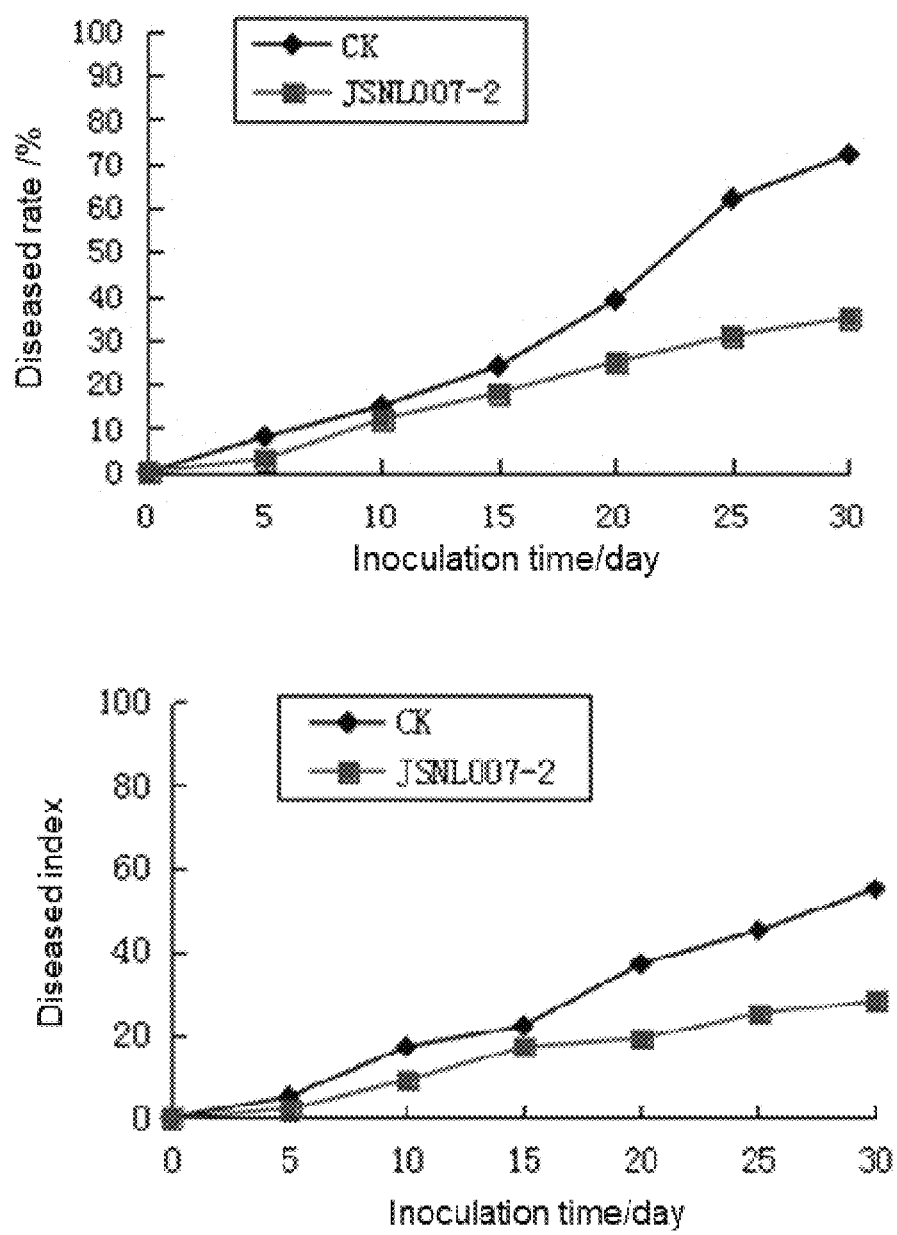
FIG. 2 is an analysis diagram of the ability of mycorrhizal *Dendrobium officinale* Kimura et Migo to resist southern blight disease with the strain JSNL007-2 of the present invention.

The diseased rate and diseased index of the test plants not inoculated with JSNL007-2 and the plants inoculated with JSNL007-2 inoculant are shown in FIG. 2.

It can be seen from FIG. 2 that within 30 days after artificial inoculation, the diseased rate and diseased index of *Dendrobium officinale* Kimura et Migo inoculated with *Fusarium solani* JSNL007-2 inoculant are significantly lower than those inoculated without *Fusarium solani* JSNL007-2 inoculant.

What is claimed is:

1. A method for improving the resistance of *Dendrobium officinale* Kimura et Migo plants to southern blight disease comprising a step of administrating an effective amount of a microbial inoculant comprising *Fusarium solani* to a *Dendrobium officinale* Kimura et Migo plant subject in need of improving resistance to southern blight disease.

2. The method according to claim 1, wherein the plant subject is a surface of a *Dendrobium officinale* Kimura et Migo seedling, and the effective amount of the microbial inoculant is 5-8 grams per the *Dendrobium officinale* Kimura et Migo seedling.

3. The method according to claim 2, wherein relative water content of the plant is maintained above 60% for 6-10 days after the microbial inoculant is administrated on the surface of the *Dendrobium officinale* Kimura et Migo seedling.

4. The method according to claim 1, wherein the *Fusarium solani* is *Fusarium solani* strain JSNL007-2, which has been deposited in China Center for Type Culture Collection on Mar. 10, 2017 with a deposit number of CGMCC NO. 13687.

* * * * *